United States Patent [19]

Lerman et al.

[11] Patent Number: 4,628,916

[45] Date of Patent: Dec. 16, 1986

[54] BRACES FOR PREVENTING INJURIES TO THE KNEE JOINT

[75] Inventors: Max Lerman, Beverly Hills; Vick G. Bonessa, Arcadia, both of Calif.

[73] Assignee: United States Manufacturing Co., Pasadena, Calif.

[21] Appl. No.: 744,500

[22] Filed: Jun. 13, 1985

Related U.S. Application Data

[63] Continuation-in-part of Ser. No. 635,815, Jun. 30, 1984, abandoned.

[51] Int. Cl.⁴ .............................................. A61F 3/00
[52] U.S. Cl. ................................. 128/80 C; 623/39
[58] Field of Search ................. 128/80 C, 80 F, 80 R, 128/88; 3/22; 403/54, 62; 623/39

[56] References Cited

U.S. PATENT DOCUMENTS

| | | | |
|---|---|---|---|
| 3,786,804 | 1/1974 | Lewis | 128/80 C |
| 3,817,244 | 6/1974 | Taylor | 128/80 C |
| 3,901,223 | 8/1975 | May | 128/80 F |
| 4,372,298 | 2/1983 | Lerman | 128/80 C |

FOREIGN PATENT DOCUMENTS

| | | | |
|---|---|---|---|
| 1187444 | 3/1959 | France | 3/22 |
| 1316572 | 5/1973 | United Kingdom | 3/22 |

*Primary Examiner*—Clifford D. Crowder
*Attorney, Agent, or Firm*—Christie, Parker & Hale

[57] ABSTRACT

Several knee stabilizing braces include an articulated knee joint support having upper and lower support arms, a first hinge bar pivoting on the upper and lower support arms and extending diagonally between them, and a second hinge bar pivoting on the upper and lower support arms and extending diagonally in an opposite direction for intersecting the first hinge bar. The two hinge bars allow relative rotation of the support arms while resisting relative forward or rearward sliding motion of each arm. Adjacent ends of the arms rotate into contact when they rotate to an upright position to stop further rotation beyond the upright position. One preventive knee brace has the upper and lower arms releasably affixed to flexible cuffs wrapped around the patient's upper and lower leg to hold the brace adjacent the knee joint. In another brace, each knee joint support is enclosed within a flexible sleeve; the support arms extend into pockets of padding, and a central sleeved portion of the padding covers the hinged portion of the brace. Flexible extensions from the padding provide infinitely adjustable attachment to the patient's legs. Another brace providing greater support includes flexible cuffs extending around the upper and lower legs, and semi-rigid reinforcing members on the cuffs, with the support arms of the braces rigidly affixed to sides of the reinforcing members. The braces are made of lightweight but rigid plastic and are offset at the hinge bars. The hinge bars are non-pinching during rotation, and reinforcing embossments in the offset regions of the arms add rigidity to reduce bending during use.

27 Claims, 15 Drawing Figures

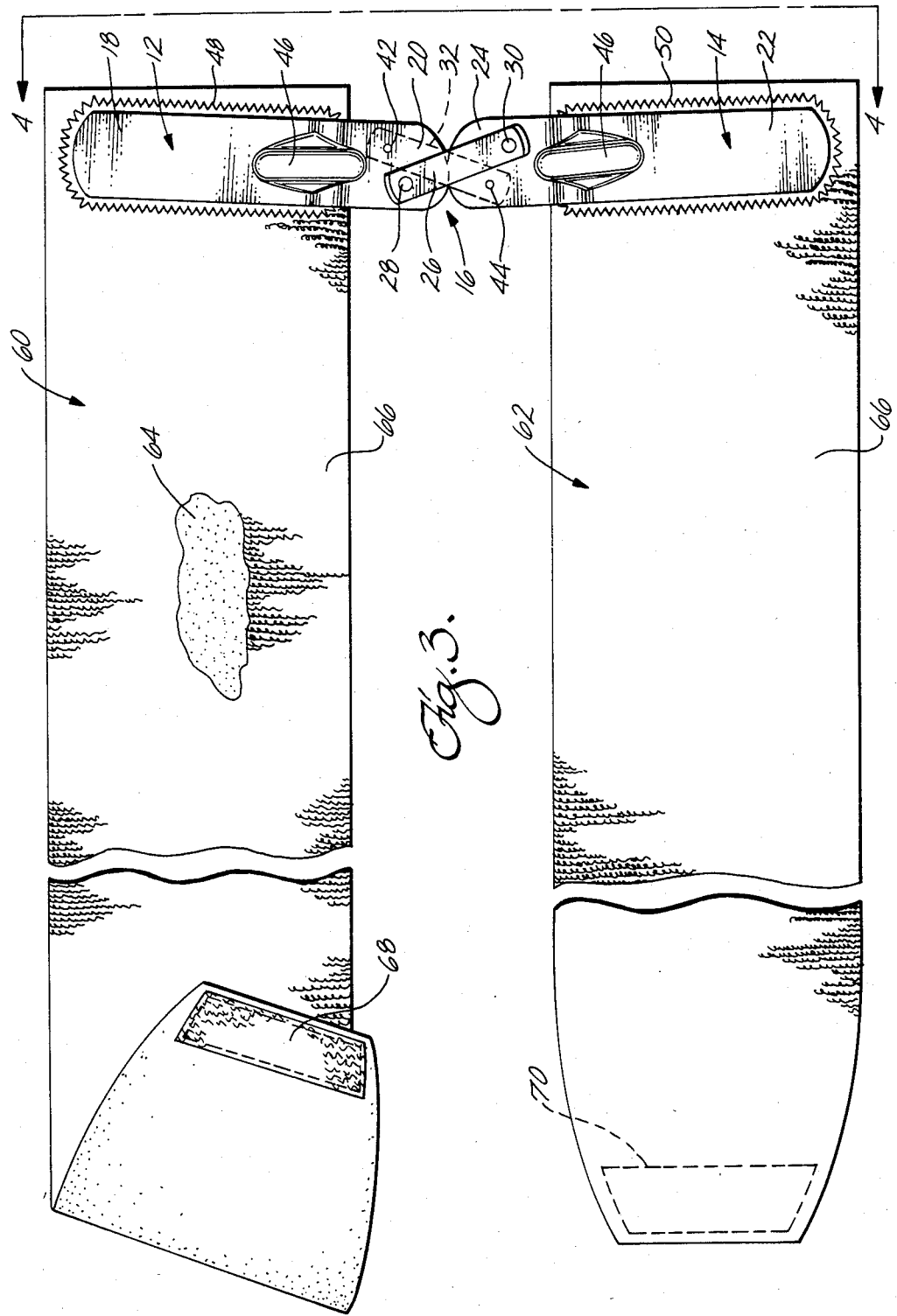

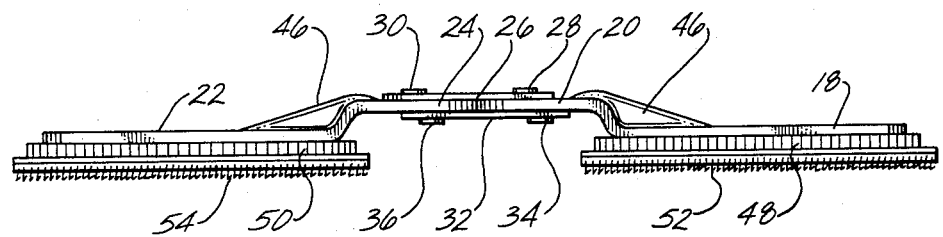
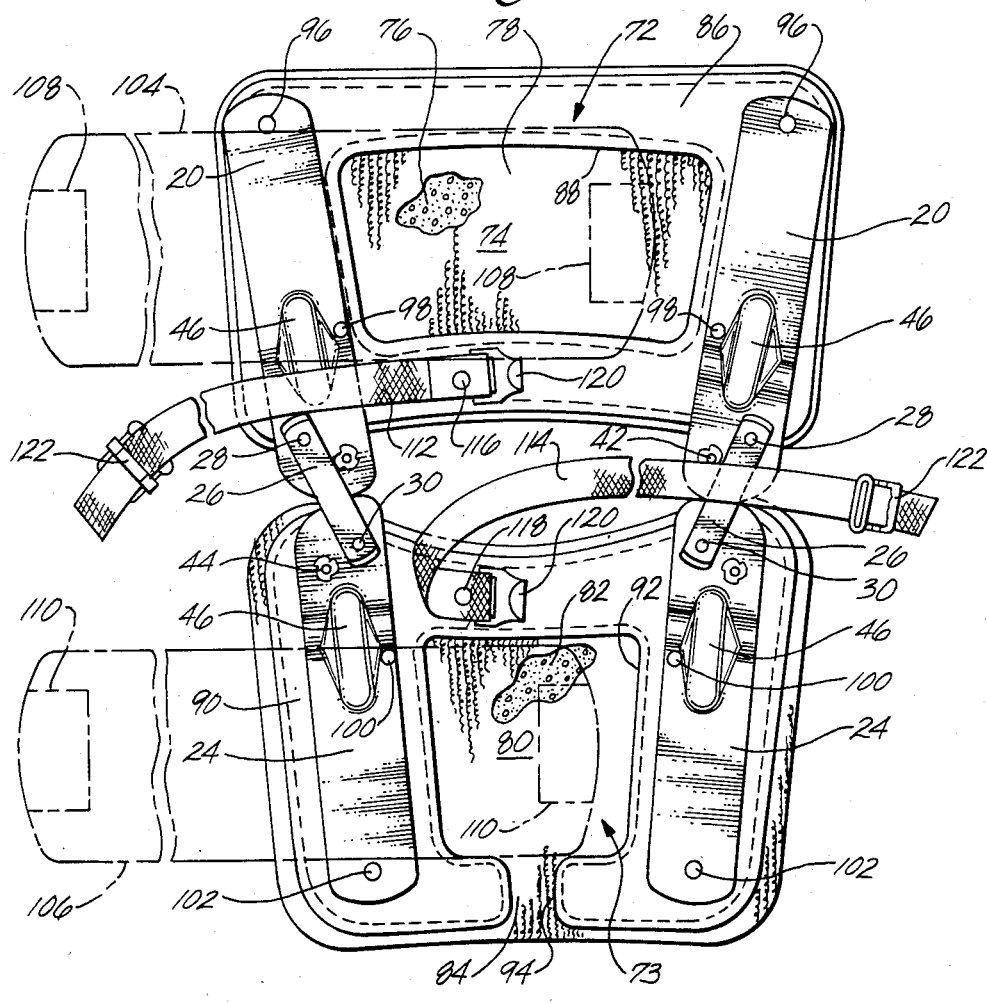

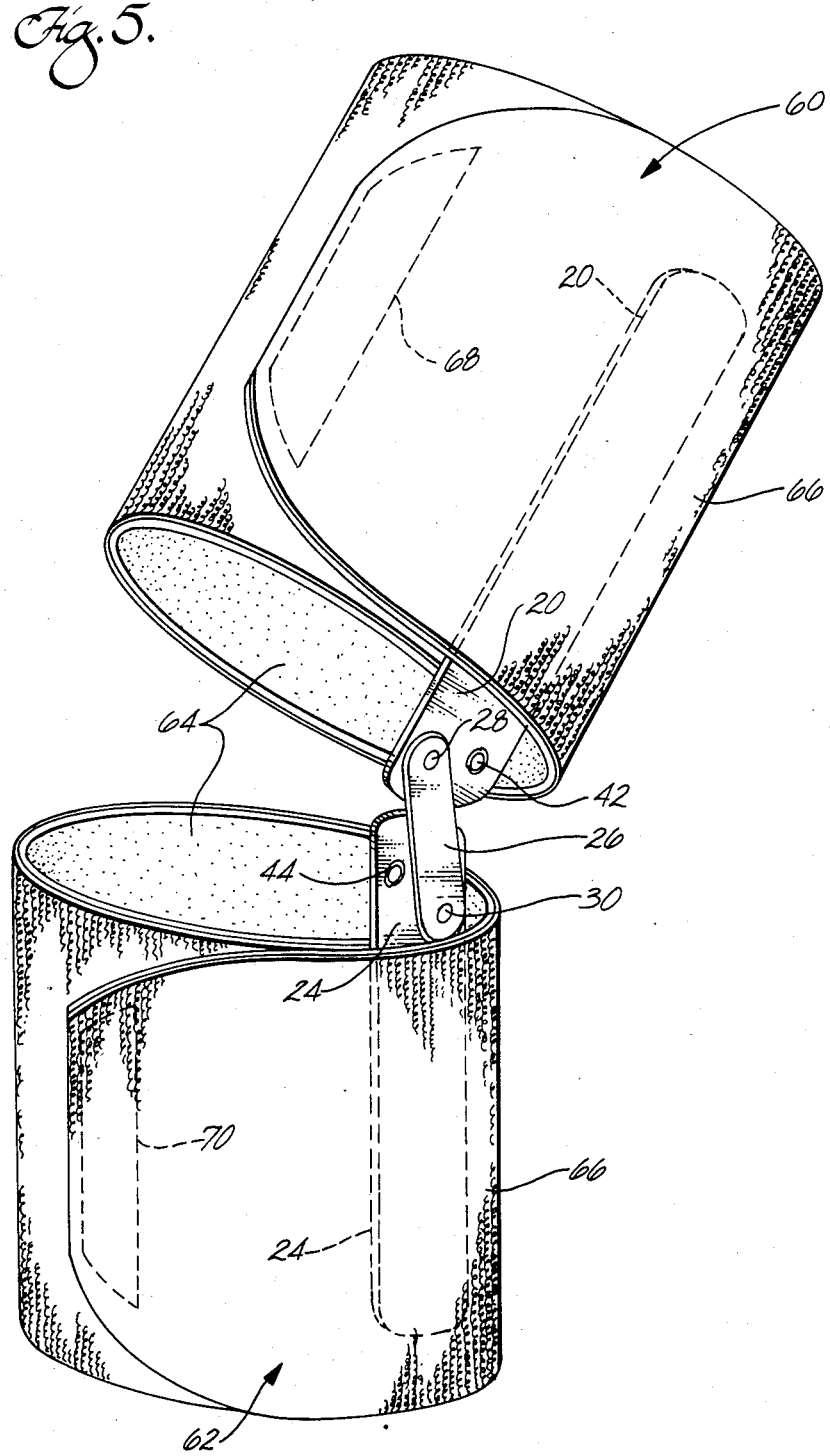

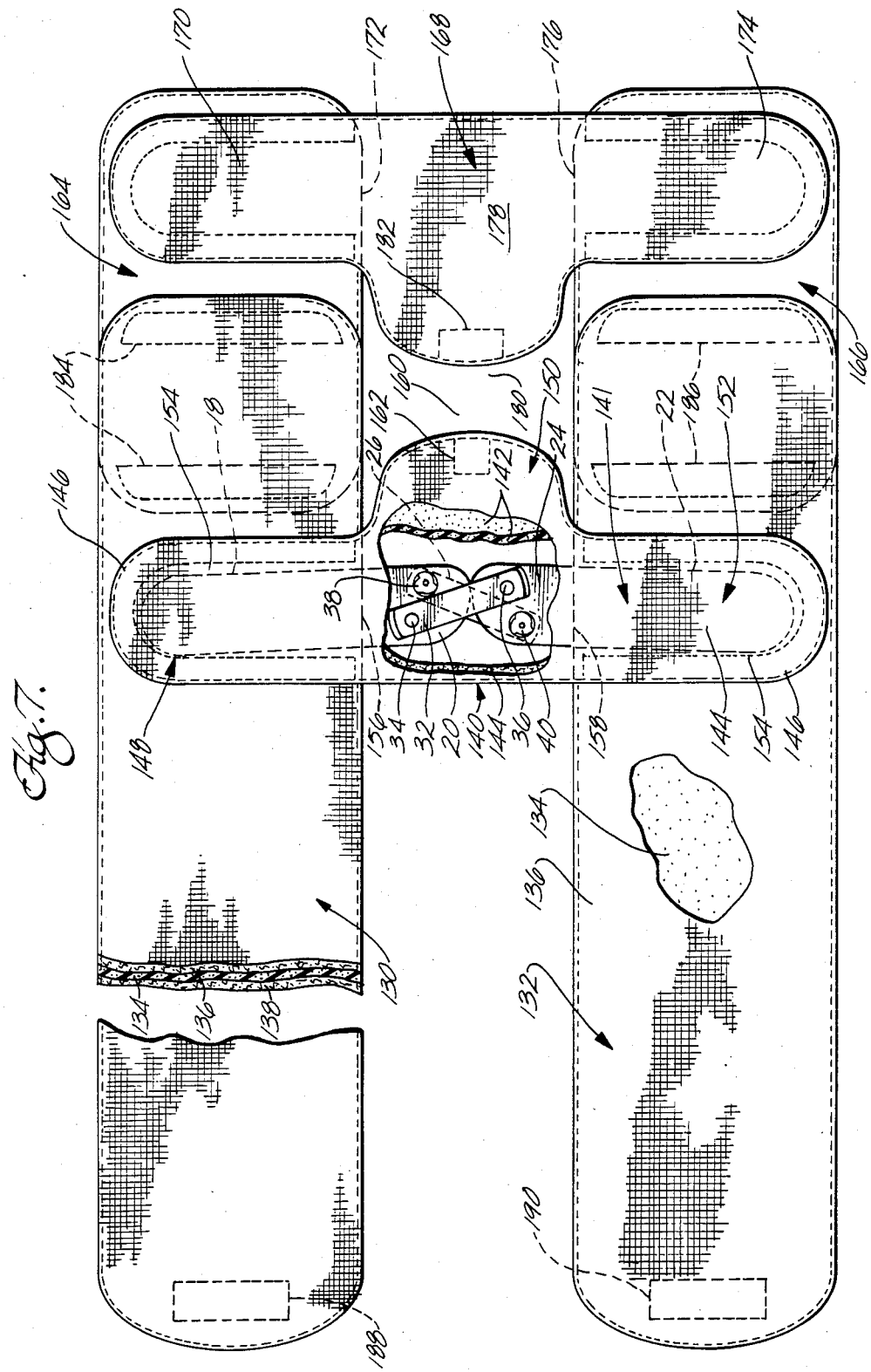

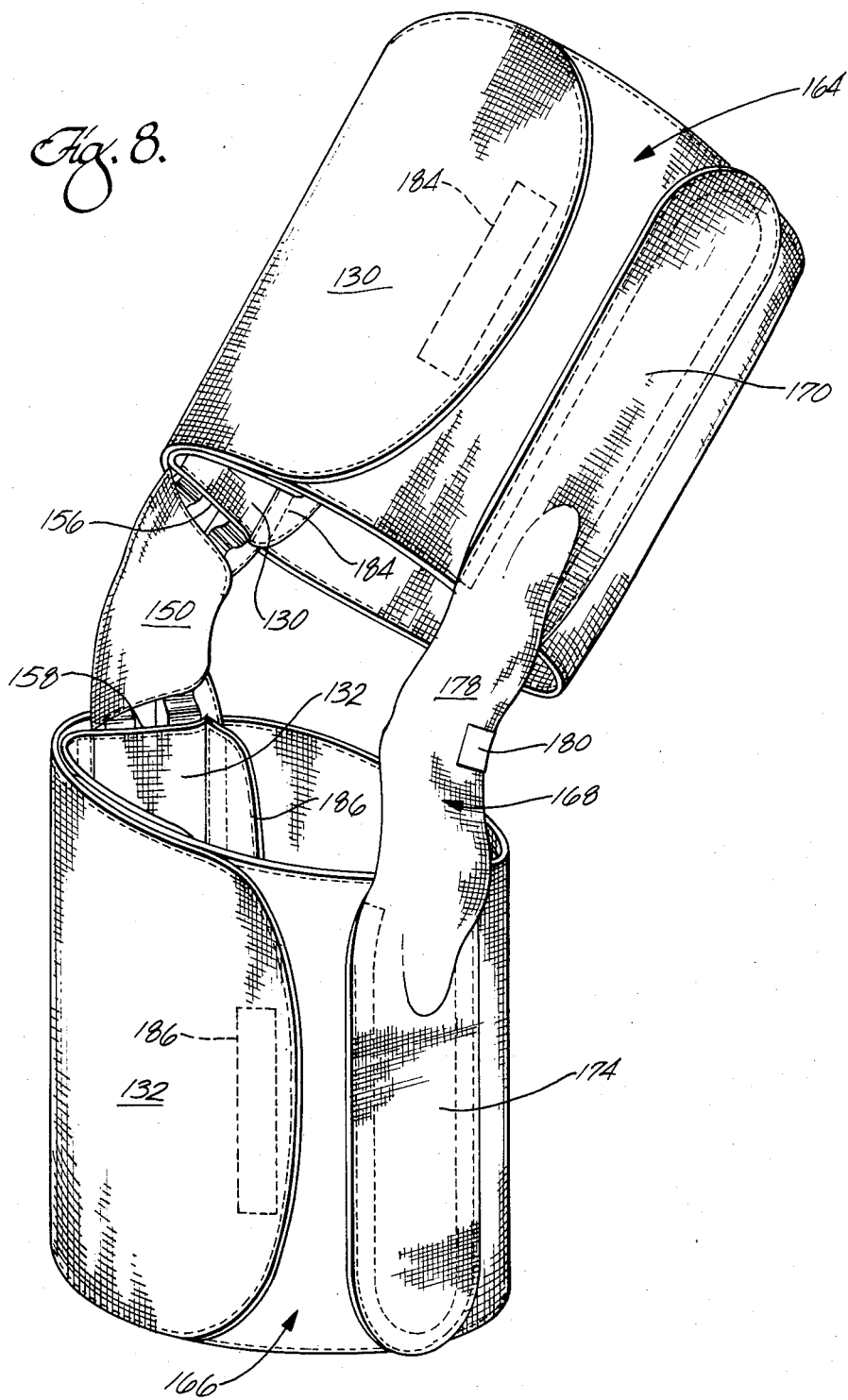

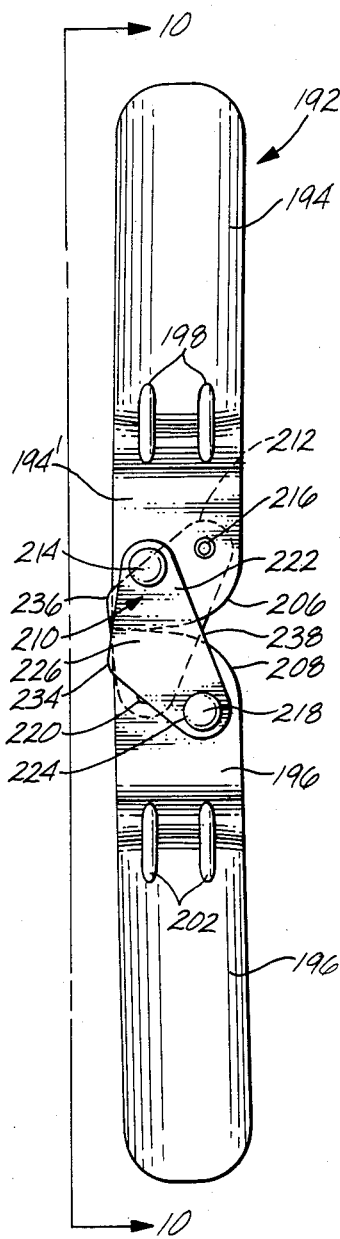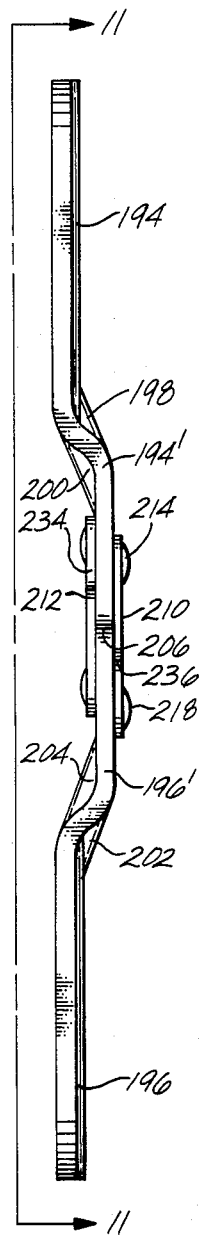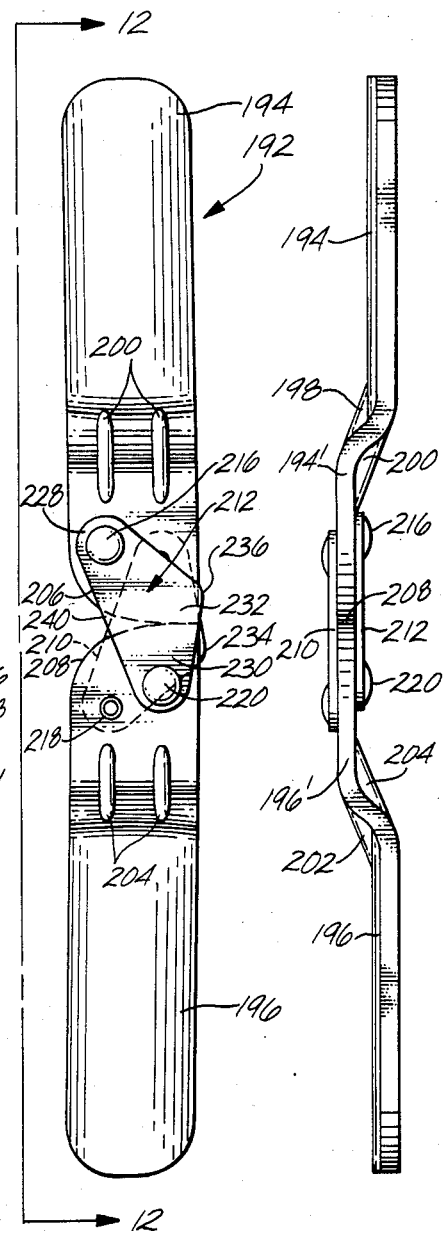

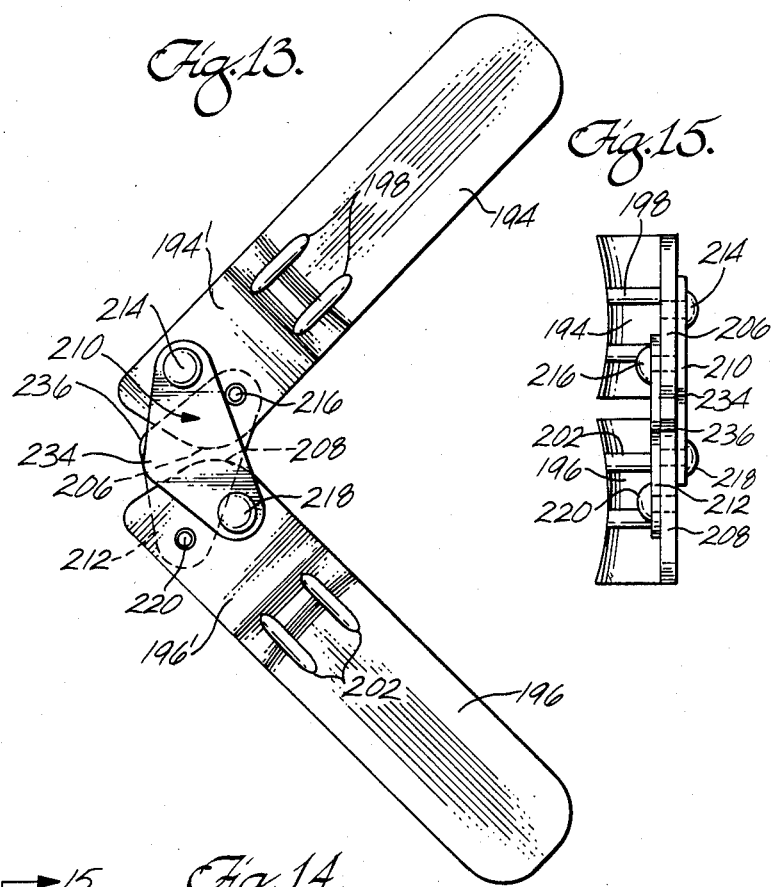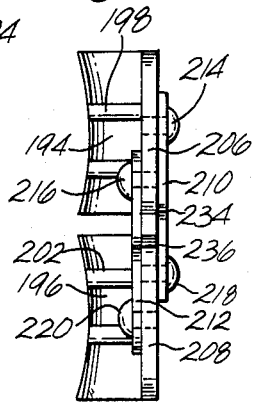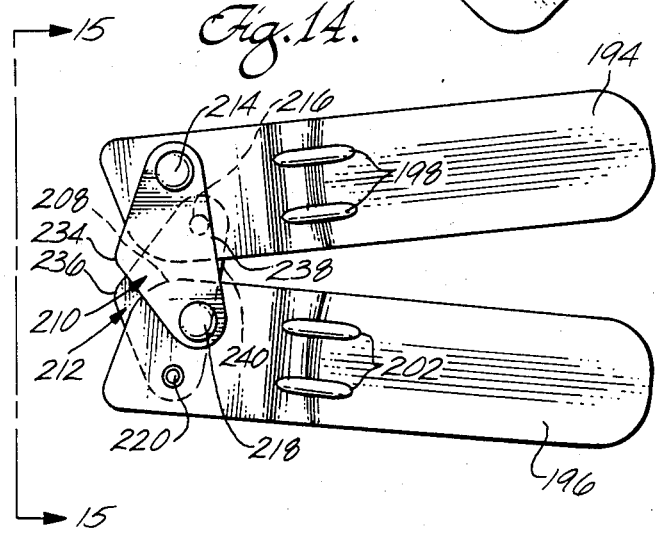

BRACES FOR PREVENTING INJURIES TO THE KNEE JOINT

CROSS REFERENCE

This is a continuation-in-part of application Ser. No. 635,815, filed July 30, 1984, now abandoned.

FIELD OF THE INVENTION

This invention relates to knee braces, and more particularly to a variety of braces for providing different levels of support to the knee joint to prevent certain motion of the knee joint that could injure the ligaments of the knee, while allowing the knee to otherwise bend safely about the normal pivot axis through the knee. In particular, the invention provides an articulated knee joint support that can be used as a component in several types of knee braces to be worn depending upon the level of protection desired. Braces are disclosed for protecting against knee injuries during sports activities, for providing protection if the knee joint is weakened either from congenital defects or from minor injuries such as sprains, or for providing a greater level of support than that offered by commonly available elastic or neoprene supports.

BACKGROUND OF THE INVENTION

A knee brace can be worn by a post-operative patient who has had knee surgery. Knee braces also can be worn by persons who suffer knee instabilities or other persons engaged in sports activities to prevent injuries to the knee. The common purpose of a knee brace is to provide exterior support for the knee to prevent any unnatural movements of the knee joint which could injure or reinjure the knee ligaments, while allowing the normal swinging movement of the knee joint about a horizontal axis through the knee (viz., forward and backward movement of the lower leg or tibia relative to the upper leg or femur, as in a normal walking motion). One type of motion to be prevented by a knee brace is a sudden movement of the upper and lower legs to one side or the other. Another type of motion to be resisted is a twisting or rotation of either the upper leg or the lower leg relative to the other about a vertical axis.

Several knee braces used for post-operative patients have been developed in recent years. These prior art knee braces include the braces disclosed in U.S. Pat. No. 3,669,105 to Castiglia and U.S. Pat. No. 4,372,298 to Lerman. Both of these braces are primarily considered to be post-operative braces intended to be fitted by an orthosist who carefully shapes the brace to the patient's lg. In fact, the Castiglia brace is custom fitted to a plaster cast of the patient's leg. Both braces are therefore accurately fitted by a skilled professional for providing rigid contact with both sides of the knee through the full range of knee motion. The required support throughout the full range of motion at the knee is needed to protect the knee joint during the post-operative rehabilitation period.

Separate and apart from post-operative knee braces, there is also a need for a lighter weight, less expensive and more comfortable brace that can be worn as an interim brace after an initial post-operative rehabilitation period, in order to continue providing protection for the knee joint as it heals.

There is also a need for a lighter weight more comfortable and less expensive preventive knee brace, one that can be worn during sports activities to prevent injuries to the knee. Similar knee braces also are needed for preventing injuries or undue stress on the knee joint for those persons who have weak knee joints possibly caused by arthritis, congenital defects, a sprained knee joint, or possibly less severe strains to the ligaments of the knee.

Sports injuries are a common cause of injuries to the knee ligaments, especially sports such as football and basketball. Players who play football at the college and professional levels are especially susceptible to knee injuries when playing on artificial turf. In recent years some football and basketball players who have had knee surgery have worn knee braces in games to allow the players to resume play earlier and to protect their knees from further injury. Such knee braces are usually rather large and bulky, and they restrict the athlete's performance to some extent. It would be desirable to provide a prophylactic knee brace that can be worn by such athletes in games and in practice to prevent injuries from occurring in the first place. The need for such a preventive knee brace extends to persons with knee problems who are engaged in a wide variety of recreational sports. The present invention provides a preventive knee brace which is light in weight and does not restrict the normal motion of the knee joint, so the athlete can perform at his or her best even though wearing the brace. Moreover, the knee brace is able to absorb the impact of a blow from different directions, while preventing undue sideways motion of the knee, twisting of the knee, or forward or rearward sliding movement of either the upper leg or the lower leg relative to the other.

One prior art knee brace that has been used for preventing sports injuries is the knee stabilizer disclosed in U.S. Pat. No. 4,249,524 to Anderson. The knee stabilizer disclosed in that patent has metal uprights for extending along the sides of the upper and lower legs, and a single metal support bar that pivots freely to each of the uprights. The brace protects against undue sideways motion of the knee joint from an impact to the side of the knee, as well as protecting against twisting of the knee. However, inasmuch as both ends of the support bar pivot freely to the upper and lower uprights, this free pivoting motion cannot prevent undue sliding motion of the upper leg relative to the lower leg, or vice versa, from impacts coming from the front or rear of the leg. The knee joint of a football player is especially susceptible to blows from the front of the knee, but the knee stabilizer disclosed in the Anderson patent cannot prevent undue stress on the knee ligaments in those situations.

One embodiment of this invention provides a preventive knee brace that is especially useful for athletes to wear in practice or in a game, without causing an undue restriction of the normal motion of the knee. The brace is light in weight and protects against the common causes of knee injuries by preventing undue stress on the knee joint from impacts at the side of the knee, or from the front or rear of the knee, as well as protecting against undue twisting of the knee joint. The knee brace is especially useful in preventing hyperextension of the knee from an impact at the front of the knee, as well as protecting against forward or rearward sliding movement of the upper leg relative to the lower leg, or vice versa. It should be emphasized that lateral impact stresses on the knee joint are best prevented by the knee support. A front impact that can result in hyperextension of the knee joint is prevented second bests. A rear impact stress or stresses due to rotation are prevented third best. The brace does not eliminate all front impact stresses, but it does provide stability sufficient to offer a level of protection against hyperextension injuries. The Anderson stabilizer, on the other hand, does not provide the same level or hyperextension protection because of its freely rotatable nature under a front impact.

SUMMARY OF THE INVENTION

One embodiment of this invention provides a knee joint support comprising an upper support arm, a separate lower support arm, and a first hinge bar pivotally secured to a lower portion of the upper support arm and to an upper portion of the lower support arm. A second hinge bar is pivotally secured to the lower portion of the upper support arm to pivot about an axis forward of the pivot axis between the first bar and the upper support arm. The second hinge bar also is pivotally secured to the upper portion of the lower support arm to pivot about an axis behind the pivot axis between the first hinge bar and the lower support arm. The first and second hinge bars allow relative rotation of the upper and lower support arms about a polycentric axis while resisting forward or rearward sliding movement of each support arm relative to the other. The lower and upper ends of the upper and lower support arms, respectively, are positioned so they rotate into contact with one another when relative rotation of the upper and lower support arms reaches a substantially upright position. The upper and lower support arms can be secured adjacent the upper and lower legs, with the first and second hinge bars positioned adjacent the knee joint. The support arms cooperate to protect against forward or rearward sliding movement of the upper leg relative to the lower leg, or vice versa. Contact between the lower and upper ends of the support arms can provide a stop to resist rotation of the upper and lower support arms beyond their upright positions to prevent hyperextension of the knee joint.

The knee joint support can be used in a knee brace for preventing sports injuries or the like. In one embodiment, the upper and lower support arms have lower and upper portions for being offset outwardly from the knee joint. These offset portions are hinged to each other by the first and second hinge bars to provide the protection for the knee joint. The upper and lower support arms can be made from a rigid plastic material for light weight and impact strength. The offset portions of the support arms, together with the hinging of the offset portions prevent direct impact to the side of the knee joint, while simulating the normal motion of the knee joint. This embodiment is particularly useful in being worn during sports activities without unduly restricting normal motion of the knee joint; and yet the knee brace and its hinged joint absorb side impacts and reduce the impact transferred to the knee while preventing the different undesired motions of the knee joint.

Another embodiment of the invention provides a highly flexible, lightweight knee brace that is comfortable to wear both as a post-operative brace (during the later stages of rehabilitation) and as a preventive knee brace. The entire knee support, including its upper support arm, its lower support arm, and the knee joint simulating hinging means is enclosed within a flexible and protective outer covering to enhance the comfort of the knee brace.

In a further embodiment of the invention, the knee joint support is used in a more rigid knee brace especially useful for supporting the knee joint after an initial period of using the more rigid custom made post-operative knee braces, such as those disclosed in the patents to Castiglia and Lerman referred to above. This knee brace, in one embodiment, has the knee joint supports arranged to extend along lateral and medial sides of the knee joint. The lateral and medial supports are rigidly secured to bendable, semi-rigid upper and lower leg supports. Each leg support is a composite support including a flexible supporting material that wraps around the upper and lower leg, and semi-rigid lightweight generally rectangular support members rigidly affixed and extending around the periphery of the upper and lower flexible supports. The knee joint supports are rigidly affixed to the rectangular semi-rigid members, and separate upper and lower cuffs are secured to the upper and lower leg supports for attaching the upper and lower portions of the brace to the leg. This brace provides a good level of protection to the knee joint especially for knee injuries or degenerative knee problems; and yet the brace is light in weight and comfortable for being worn for a long period of time.

In a further embodiment of the invention, the upper and lower support arms of the knee joint support pivot through a pair of non-pinching hinge bars. The hinge bars extend over the space between the adjacent ends of support arms, and the bars pivot relative to each other to avoid pinching objects entering the space between the ends of the support arms.

These and other aspects of the invention will be more fully understood by referring to the following detailed description and the accompanying drawings.

DRAWINGS

FIG. 3 is a fragmentary side elevation view showing the knee joint support used in a lightweight, impact-resisting protective knee brace especially useful in preventing injuries to the knee during sports activities.

FIG. 4 is a side elevation view taken on line 4—4 of FIG. 3.

FIG. 5 is a perspective view of the knee brace shown in FIG. 3.

FIG. 6 is a fragmentary front elevational view showing an alternative knee brace of this invention unfolded into flat form; this knee brace is a more rigid brace using the knee joint supports of this invention to provide a brace especially useful for knee injuries or degenerative knee problems, although it can also be worn by post-operative patients.

FIG. 7 is a side elevation view showing a further alternative knee brace embodiment of this invention; this knee brace is an entirely flexible lightweight comfortable knee brace that can be used as a protective device or for post-operative use.

FIG. 8 is a perspective view showing the knee brace of FIG. 7.

FIG. 9 is a side elevation view showing a knee joint support having non-pinching hinge bars according to principles of this invention.

FIG. 10 is an end elevation view taken on line 10—10 of FIG. 9.

FIG. 11 is an elevation view of an inside face of the knee joint support taken on line 11—11 of FIG. 10.

FIG. 12 is an end elevation view taken on line 12—12 of FIG. 11.

FIG. 13 is a side elevation view of the knee joint support of FIGS. 9 through 12 showing the support arms rotated to a first angular position.

FIG. 14 is a side elevation view of the knee joint support showing the support arms rotated to a second angular position.

FIG. 15 is an end elevation view taken on line 15—15 of FIG. 14.

DETAILED DESCRIPTION

Figure 1:
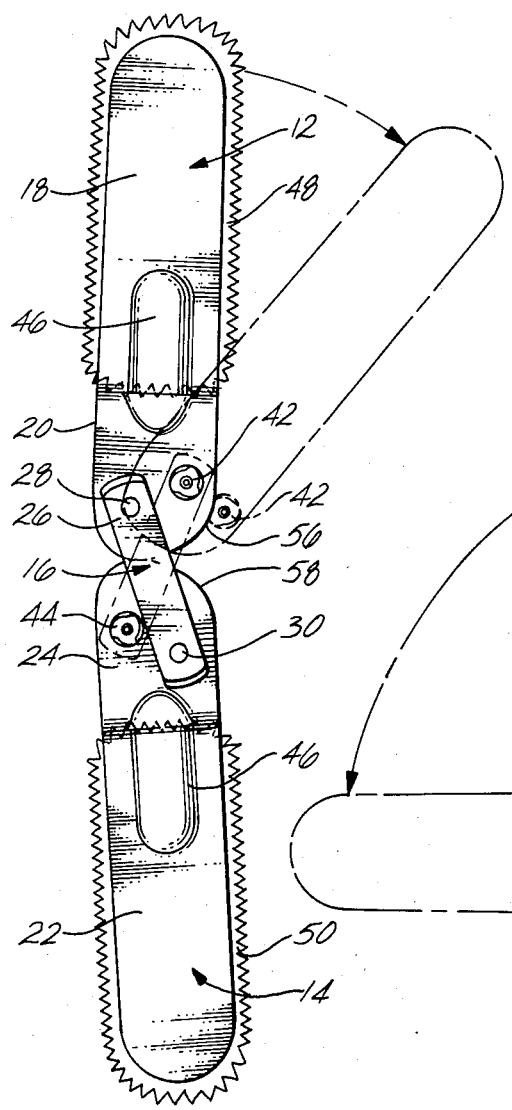
FIG. 1 is a side elevation view showing the outside face of a knee joint support according to the principles of this invention.
Figure 2:
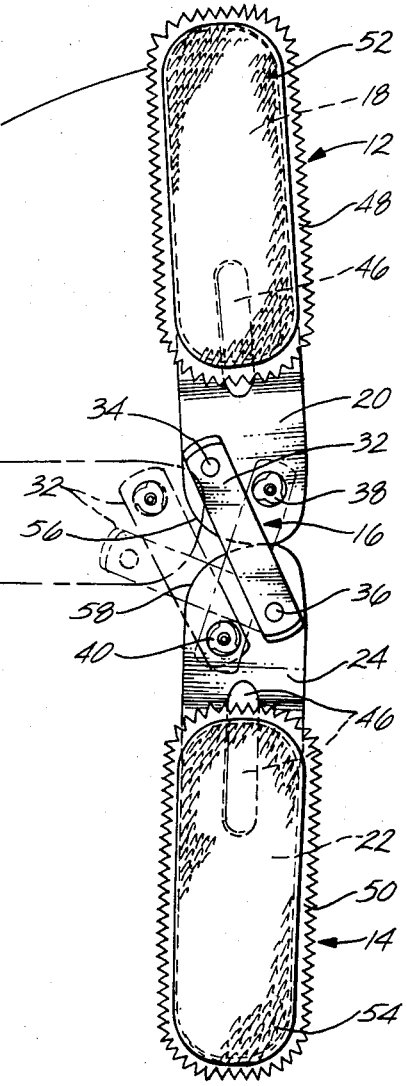
FIG. 2 is a side elevation view showing the inside face of the knee joint support shown in FIG. 1.

FIGS. 1 and 2 illustrate an articulated knee joint support having an elongated upper support arm 12 and a similar elongated lower support arm 14. The support arms are pivotally interconnected at their adjacent ends by X-shaped hinge means 16 described below. The upper support arm 12 is a relatively wide and thin rigid member adapted to overlie the outside of the upper leg immediately above the knee joint. The lower support arm 14 is a similar relatively wide and rigid member adapted to overlie the outside of the lower leg immediately below the knee joint. The upper support arm has a long, relatively thin and flat upper portion 18 and a laterally offset lower portion 20 which is also thin and flat but spaced outwardly from the plane of the upper portion 18. The upper support arm thus has a stepped region at the interface between its upper portion and offset lower portion. The lower support arm 14 has a long, relatively thin and flat lower portion 22 and a laterally offset upper portion 24 which is also thin and flat and spaced laterally outwardly from the plane of the lower portion 22. The lower arm has a stepped region between the lower portion and offset upper portion of the lower support arm. The upper and lower support arms are preferably made from a rigid lightweight material having impact resistant properties, and a preferred material is polypropylene.

The X-shaped hinge 16 includes an elongated flat rigid first stabilizing hinge bar 26 extending diagonally between the lower portion 20 of the upper support arm 12 and the upper portion 24 of the lower support arm 14. A front pivot pin 28 pivotally connects the first hinge bar 26 to a front portion of the upper support arm, and a rear pivot pin 30 pivotally connects a lower portion of the first hinge bar to a rear portion of the lower support arm 14.

As shown best in FIG. 2, the X-shaped hinge 16 also includes an elongated flat rigid second stabilizing hinge bar 32 extending diagonally between the lower portion 20 of the upper support arm 12 and the upper portion 24 of the lower support arm 14. An upper pivot pin 34 pivotally secures an upper portion of the second hinge bar to the rear of the offset lower portion 20 of the upper bar 12. A lower pivot pin 36 pivotally secures the lower portion of the second hinge bar 32 to a forward region of the offset upper portion 24 of the lower support arm 14. The first and second hinge bars are on opposite sides of the offset portions of the upper and lower support arms.

Thus, when the knee supporting brace is viewed from the side as in either FIG. 1 or FIG. 2, the axes of the two hinges bars intersect to form the X-shaped hinge. The first hinge bar overlies the outer faces of the lower and upper offset portions of the upper and lower support arms, respectively; and the second hinge bar overlies the inside faces of the offset lower and upper portion of the upper and lower support arms, respectively. The first and second hinge bars are preferably made of a rigid metal such as stainless steel.

The preferred means for pivoting the stabilizing hinge bars to the upper and lower support arms include upper and lower T-nuts 38 and 40 (see FIG. 2) with prongs embedded in the plastic that forms the upper and lower support arms. The prongs prevent the T-nuts from rotating relative to the support arms. The pivot pins 28 and 30 that attach the first stabilizing bar 26 to the support arms extend through holes drilled in the stabilizing bar and then into receptacles in the T-nuts in a press fit so that the first stabilizing bar 26 can rotate relative to its pivot pin means of attachment to the upper and lower support arms. Similarly, the second stabilizing bar 32 is pivotally attached to the upper and lower support arms by T-nuts 42 and 44 embedded in the plastic lower and upper portions of the upper and lower support arms, respectively. The upper and lower pivot pins 34 and 36 are press-fitted into these T-nuts to allow the second stabilizing bar 32 to pivot relative to its fixed means of pivotal attachment to the upper and lower support arms. The T-nuts are embedded in the plastic so that the flanged portions of the T-nuts are at or below the planar outer faces of opposite sides of the upper and lower support arms. Thus, as the upper or lower support arms pivot, the first or second stabilizing bars can easily slide over the exposed outer surfaces of the flanged portions of the T-nuts that hold the opposite stabilizing bars.

The upper and lower support arms are each reinforced by an elongated molded plastic embossment 46 that extends from the principal portion of the support arm, across the stepped region of the support arm, to the offset portion of the support arm. The embossments project outwardly from the outer face of the support arm and are recessed inwardly on the inner face of the support arm. The embodiments are the same wall thickness as the rest of the support arm. The embossment projects from the face of the principal portion of each support arm and from the face of the offset portion of each support arm. The depth of the embossment is the largest in the stepped region of the support arm. The reinforcing embossments provide lateral rigidity to the support arms in the sense that they restrict bending of the offset portions of the bars relative to the principal portions of the bars about an axis extending the length of the support arms. The reinforcing embossments provide the level of rigidity necessary for the support arms to act as lightweight impact-resistive members that prevent the transfer of impact to the ligaments of the knee joint during use. A similar knee brace without such reinforcing embossments has been found to be too flexible and therefore transfers a substantial amount of the impact blow to the side of the knee joint as opposed to resisting a useful level of impact energy.

The metal stabilizing bars each overlie a substantial length of the adjacent offset portions of the upper and lower support arms in the hinged areas of the arms. The rigidity of the hinge bars adds further reinforcing to the support arm to resist the transfer of impact energy to the side of the knee joint during use.

The upper and lower support arms have respective upper and lower layers 48 and 50 of padding. The padding is preferably made from a compressible plastic foam material. In one embodiment the layers of padding are provided by a closed cell foam such as Plastizote, although the padding also can be provided by an open cell foam such as polyurethane foam. The layer of padding are affixed to the inside faces of the principal portions of the support arms, leaving the stepped regions and the hinged offset portions of the brace free of such padding. The layers of padding are preferable affixed to the support arms by adhesive bonding.

Elongated upper and lower sections 52 and 54 of thistle cloth fasteners are secured to the outer faces of the upper and lower layers of padding, respectively. In the illustrated embodiment the layers of fastening material are a hook-type fastener sold under the trademark Velcro. The upper and lower thistle cloth fasteners 52 and 54 are preferably in flexible strip form attached to the padding by rows of stitching.

The hinged stabilizing bars 26 and 32 allow the upper or lower support arms to pivot relative to the other support arms, as illustrated for example by the arc shown in phantom lines in FIGS. 1 and 2. The X-shaped hinge allows either support arm to pivot from the fully upright position shown in FIGS. 1 and 2 through an arc as great as 180 degrees relative to the other support arm. The X-shaped hinge bars also provide relative stability during the angular travel of either support arm by preventing forward or rearward sliding movement of either bar relative to the other bar throughout the full range of angular motion between the two support arms.

The upper support arm 12 has a curved bottom edge 56 and the lower support arm 14 has a curved top edge 58. Both edges engage one another when the support arms are both in a generally upright position shown in solid lines in FIGS. 1 and 2. In this substantially upright relative position the long axes of the two support arms are aligned in essentially a vertical axis, although each arm may extend at an angle of about 86 to 88 degrees rather than a true right angle with respect to a horizontal axis extending through their point of contact. Both adjacent curved edges taper away from one another in the direction toward which each arm is free to rotate. This gradually widened tapered open space between the adjacent edges of the arms allows each arm to pivot through a full 180 degree angle relative to the other arm, or allows the two arms to pivot together through combined angles that total 180 degrees. For instance, the upper arm can pivot 90 degrees relative to the lower arm, as illustrated in FIG. 2; and the lower arm then can pivot up to the other arm until the two arms extend essentially parallel to one another, i.e., each as rotated through an angle of about 90 degrees.

The two adjacent curved edges 56 and 58 are configured so that they rotate into rigid engagement with one another as the two arms rotate toward the vertical upright position shown in FIGS. 1 and 2. As the two arms arrive at this angular orientation with respect to one another the two curved edges come into contact and prevent further rotation of either arm relative to the other. That is, in the arrangement shown in FIG. 1, the upper arm 12 can rotate clockwise, to the right in the direction of the arrow; but when rotating in the opposite direction the arm is stopped by contact between its bottom edge and the top edge of the lower arm, stopping in the upright position shown. The same is true for the bottom support arm in that it may rotate to the left in a counterclockwise direction; but when rotating toward the upright position shown in FIG. 1 its top edge comes in contact with the curved bottom edge of the upper support arm; and this mutual contact prevents further rotation of the lower arm in the clockwise direction. By thus limiting rotation of the two support arms past their substantially upright positions, the knee joint support shown in FIGS. 1 and 2, when used in a knee brace according to principles of this invention, can prevent hyperextension injuries to the knee joint as described in greater detail below.

FIGS. 3 through 5 illustrate a knee brace made from the knee joint support shown in FIGS. 1 and 2. The knee brace includes an elongated flexible and stretchable upper cuff 60 and a similar flexible and stretchable lower cuff 62. Each cuff preferably has a thin inside layer 64 of neoprene rubber and an outer layer of a pile-type fabric material such as terry cloth which also has an exceedingly high frictional adherence to Velcro-type hook fastener material. As shown best in FIG. 3, the Velcro hook fasteners 52 and 54 of the upper and lower support arms are releasably secured to the terry cloth outer layers 66 of the upper and lower flexible cuffs. The free end of the upper cuff has an elongated section 68 of a Velcro-type hook fastener material, and the free end of the lower cuff 62 has a similar section 70 of a Velcro-type hook fastener material.

The knee brace shown in FIGS. 3 through 5 is a lightweight impact protective knee brace especially useful in protecting against knee injuries in sports such as football and basketball. The knee brace is used by attaching the Velcro fasteners 52 and 54 on the insides of the upper and lower support arms to end regions of the upper and lower cuffs as shown in FIG. 3. The upper and lower support arms are then positioned along the lateral (outer) sides of the upper and lower legs so the hinge joint is positioned adjacent the lateral side of the knee joint. In the knee brace shown in FIG. 3, the knee support is positioned on the left leg so that the upper and lower support arms will pivot to the right in FIG. 3 during flexion of the knee joint and will stop in the upright positions shown in FIG. 3 during extension of the knee joint. After positioning the knee support adjacent the lateral side of the upper and lower legs, the upper and lower cuffs are then wrapped tightly around the upper and lower legs to hold the knee supporting brace in place adjacent the lateral side of the knee joint. The upper and lower cuffs are wrapped entirely around the upper and lower legs and around the outside of the upper and lower support arms of the knee joint support. The fasteners 68 and 70 at the free ends of the cuffs are then attached to the fabric layers 66 of the cuffs to retain the tension around the legs provided by each cuff.

During use, the hinged portion of the knee joint support is offset outwardly from the side of the knee joint so that any impact in this area is not transferred directly to the side of the knee joint. Any impact to the lateral sides of the upper or lower legs also is resisted by the impact protective upper and lower support arms. The hinged joint 16 is a polycentric hinge that closely simulates the natural angular motion of the knee joint, and the knee brace being light in weight and being able to simulate normal knee joint motion makes it possible to use the brace during sports activities without significant interference with the athletes performance. The support provided by the knee brace resists sideways motion of the knee joint from a blow to the side of the knee joint; it resists twisting of the lower leg relative to the lower leg or vice versa; and it resists forward or rear sliding motion of either the upper or lower leg relative to the other. It also prevents hyperextension of the knee joint from an impact at the front of the knee joint. The stop provided by the contacting adjacent edges of the support arms inhibits hyperextension of the knee joint.

FIG. 6 illustrates an alternative knee brace used primarily for patients who need a greater amount of support for the knee joint during a post-operative rehabilitation period, but less support and more comfort than is provided by the more rigid custom fitted knee braces such as the Castiglia or Lerman braces described above. The knee brace includes a semi-rigid bendable upper cuff 72 for overlying the front half of the upper leg above the knee joint and a semi-rigid bendable lower cuff 73 for overlying the front half of the lower leg below the knee joint. The upper cuff comprises an elongated generally rectangular piece of flexible padding 74 having a resilient, flexible, stretchable interior layer 76 such as neoprene rubber with an outer protective layer 78 of a flexible fabric that attaches to a Velcro-type hook fastener material. The preferred exterior fabric layer 78 is terry cloth similar to that used for the upper and lower cuffs of the brace shown in FIGS. 3 through 5. The interior layer of the upper cuff 72 is preferably provided by any flexible comfortable fabric such as cotton or velour.

The lower cuff 73 is of similar construction to the upper cuff 72 and includes a flexible, resilient and stretchable composite padding 80 of generally rectangular configuration having an interior layer 82 of neoprene rubber, an outer flexible fabric layer 84 of a material such as terry cloth capable of attaching to a Velcro hook-type material, and an interior layer of a fabric such as cotton or velour.

The upper cuff 72 also includes a generally rectangular bendable reinforcing member 86 extending around the perimeter of the layer of padding 74, leaving a generally rectangular opening 88 in the central region of the upper cuff. The upper reinforcing member 86 is preferable made from a lightweight, semi-rigid plastic material such as polyethylene.

Similarly, the lower cuff 73 includes a generally rectangular outer reinforcing member 90 extending around the perimeter of the rectangular piece of padding 80. Each leg of the reinforcing member 90 extends along each side of the rectangular piece of padding, leaving a generally rectangular central opening 92 with a narrow open space 94 at the bottom center of the rectangular reinforcing member 90.

Separate knee joint supports similar to those shown in FIGS. 1, 2, and 4 are rigidly affixed to the reinforced opposite sides of the upper and lower cuffs. Fasteners 96 secure upper portions of the upper support arms 20 to the upper outer corners of the rectangular upper reinforcing member 86. Fasteners 98 secure intermediate inside portions of the upper support arms 12 to the side portions of the upper reinforcing member 86. The fasteners extend entirely through the plastic reinforcing members and the layer of padding inside them. Preferably the fasteners are rivets with the flanged T-nut portions of the rivet combination being on the inside of the upper cuff. Similar fasteners 100 secure lower portions of the upper support arms 24 to the lower outer corners of the rectangular lower reinforcing member 90. Fasteners 102 secure the intermediate inside portions of the lower support arms 24 to side portions of the lower reinforcing member 90.

The knee brace shown in FIG. 6 also includes upper and lower flexible straps 104 and 106, respectively, releasably securable to the upper and lower cuffs of the brace. These straps are shown in phantom lines in FIG. 6 for clarity. The upper and lower straps are stretchable longitudinally and are preferably made from a thin inner layer of neoprene rubber and an outer layer of a fabric such as terry cloth. Velcro hook-type fasteners 108 are secured to the inside face of the upper strap at its opposite ends. Similar Velcro hook-type fasteners 110 are secured to the inside face of the lower strap at its opposite ends. The Velcro hook-type fasteners can be releasably attached to the terry cloth material in the central openings 88 and 92 of the upper and lower cuffs, as illustrated in FIG. 6.

The brace also includes an upper elastic strap fasteners 112 secured to a lower portion of the upper cuff, and an elastic strap fastener 114 secured to an upper portion of the lower cuff. The upper elastic strap fastener includes a reinforced section attached to the lower portion of the upper reinforcing member 86 by a fastener 116, such as the rivets used for fastening other components of the brace to the upper cuff. Similarly, a fastener 118 rigidly affixes a reinforced section of the lower elastic fastener to the upper portion of the reinforcing member 90 of the lower cuff. Hooks 120 are carried on the reinforced fixed end portions of the elastic strap fasteners, and adjustable connectors 122 for attachment to the hooks 120 are at the free ends of the elastic strap fasteners 112 and 114.

The brace in FIG. 6 is used by placing it over the front of the upper and lower legs and bending the semi-rigid upper and lower cuffs so that the upper and lower support arms 20 and 24 of the knee joint supports extend along the lateral and medial sides of the upper and lower legs. The hinged portions of the knee joint supports are positioned adjacent the lateral and medial sides of the knee joint. The semi-rigid upper and lower reinforcing members 86 and 90 are sufficiently bendable to conform the brace easily to the shape of the upper and lower legs. The open space 94 at the center of the bottom reinforcing member removes any pressure that would otherwise be applied to the front of the shin bone by the lower cuff. The Velcro fasteners on the upper and lower straps are releasably secured to the fabric in the center of the upper and lower cuffs, and the upper and lower straps 104 and 106 are then wrapped tightly around the upper and lower legs. Because of the resilience of the and lower straps, owing to their neoprene rubber layers, the upper and lower straps can be tensioned to the desired level when wrapping them around the upper and lower legs. Once the upper and lower straps are wrapped around the legs, the Velcro hook type fasteners 108 and 110 at the free ends of the straps are adhered to the terry cloth outer layers of the straps themselves to hold the tension. The elastic strap fasteners 112 and 114 are wrapped around the patient's upper and lower legs immediately above and below the knee joint, and the desired amount of tension produced by these straps is held by connecting the fasteners 122 with the hooks 120 on the strap fasteners. This provides an additional means for holding the brace in place adjacent opposite sides of the patient's knee.

The semi-rigid upper and lower cuffs of the knee brace provide a good level of support for holding the lateral and medial knee joint supports in place on opposite sides of the knee joint. This provides an intermediate level of support that makes the knee brace particularly useful for cases in degenerative arthritis and sprains of knee. It can also be used as a post-operative brace to replace the more rigid and less comfortable custom fitted knee brace later during the rehabilitation period. This brace makes it possible for the patient to come out of the custom fitted post-operative brace at an earlier time and be able to use this brace which is much lighter in weight and more comfortable, yet provides the level of support necessary during the rehabilitation process. The semi-rigid reinforcing members provide the necessary level of firm support for the brace and also provide a means for securely holding the knee joint supports in place along opposite sides of the patient's knee during rehabilitation. The central openings of the semi-rigid reinforcing members reduce the weight of the brace, add to its comfort and flexibility, and also provides a means of releasably attaching the lightweight, comfortable, flexible upper and lower straps for securing the brace to the upper and lower legs. A brace also has the advantages provided by the knee joint supports themselves, such as the ability to resist sideways motion of the knee joint either outwardly or inwardly, resisting twisting about the knee joint, or resisting sliding movement of the upper leg in either a forward or rear directions relative to the lower leg, or vice versa, while preventing hyperextension of the knee joint.

FIGS. 7 and 8 illustrate a further alternative embodiment of the invention, namely, a highly flexible lightweight and comfortable knee brace made with the knee joint support of this invention. In this knee brace, lateral and medial knee joint supports similar to the knee joint support illustrated in FIGS. 1 and 2 are attached to upper and lower composite strap fasteners and knee joint enclosures which are entirely flexible and have no semi-rigid or rigid means of support for the leg or knee joint. The brace includes an elongated, flexible and stretchable long upper strap 130 and a similar long lower strap 132. The two straps are spaced apart and extend parallel to one another. The two straps are completely flexible with no rigid or semi-rigid means of support, and they preferably are made from a thin internal layer 134 of a stretchable material such as neoprene rubber, with inner and outer layers 136 and 138 of a flexible fabric such as terry cloth adapted to make good contact with Velcro-type hook fastener material.

An elongated flexible protective sheath or enclosure 140 extends perpendicularly between the upper and lower long straps 130 and 132. The sheath provides an enclosure for one of the knee joint supports as illustrated best in FIG. 7. The flexible sheath is preferably made from a single piece of flexible and stretchable material such as a thin inner layer 142 neoprene rubber, and an outer layer 144 of a flexible protective fabric material such as terry cloth. The two layers are stitched together about their periphery by marginal stitching illustrated at 146 in FIG. 7, for example. This stitching also provides a means for fastening the flexible enclosure to the upper and lower long straps. The flexible enclosure 140 has a narrow elongated upper portion 148 overlying the upper strap, an enlarged central portion 150 the extends over the open space between the two parallel straps, and a narrow elongated lower section 152 overlying the lower strap. In the illustrated embodiment, the flexible enclosure 140 is fastened to the upper and lower straps at a point a short distance inboard the end of the upper and lower straps, leaving most of the length of the upper and lower straps extending from its opposite side. Preferably, the enclosure is secured to the upper and lower straps at a point less than the circumferential distance from one side of the knee joint to the other side of the knee joint. The upper and lower sections of the enclosure are attached to the upper and lower straps by rows of stitching 154. The portion of the enclosure piece which extends over the adjacent portion 156 of the lower edge of the upper strap is left open rather than being attached to the strap. This forms a lower opening of a narrow, elongated pocket formed between the upper section 148 of the enclosure and the adjacent portion of the upper strap. Similarly, the lower portion 152 of the enclosure, where it extends past an upper edge portion 158 of the lower strap, also is left open to form an upper opening to a narrow, elongated pocket formed inside the region between the lower portion 152 of the enclosure and the outer face of the lower strap. These long narrow pockets provide means for slidably inserting the upper and lower support arms 18 and 22 of the knee joint support into the enclosures for retaining the knee joint support in a fixed position relative to the upper and lower straps. The support arms remain removably disposed with the long, narrow pockets during use.

The enlarged central region 50 of the flexible enclosure is widened at one side to a width about twice the width of the narrow pocket regions of the same enclosure. This provides a flexible flap of sufficient length to be folded around the rear side of the hinged portion of the knee joint support so that the flap can entirely encompass both the inside and outside of the hinged portion of the brace. The width of this enlarged region of the flexible enclosure is sufficiently oversized when the flap is folded over to leave sufficient room internally within the folded region of the enclosure so that the hinged portion brace can pivot through its normal angular travel during use without interference from the flexible enclosure. The flap on the enlarged region 150 includes an elongated strip 160 of a Velcro hook-type fastener material attached to the flexible flap by stitching 162. The hooked portion of the Velcro-type fastener faces away from the view in FIG. 7, and when the flap is folded around the rear side of the brace, the hook-type fastener material then can be frictionally attached to the terry cloth outer surface of the central portion of the flexible enclosure. This retains the flexible enclosure around both sides of the hinged portion of the brace.

The flexible protective knee brace of FIGS. 7 and 8 also includes an elongated short upper strap 164 and a similar short lower strap 166 extending parallel to one another and spaced apart by the same distance as the long upper and lower straps 130 and 132. The short upper and lower straps are made from the same material as the long upper and lower straps 130 and 132. A second flexible enclosure or sheath 168 constructed similar to the other sheath or enclosure 140 is secured to the short upper and lower straps. The second flexible enclosure 168 thus includes a narrow elongated upper section 170 forming a narrow elongated pocket with a lower opening at 172, a narrow elongated lower section 174 overlying the short lower strap and having an upper opening 176 to a narrow pocket overlying the short lower strap, and an enlarged region 178 which is enlarged in the direction of the flap formed by the enlarged section 150 of the other flexible enclosure. The second flexible enclosure 168 is made from the same material as the other flexible enclosure, and is attached to the upper and lower straps in the same way. The second flexible enclosure also includes an elongated strip 180 of a Velcro hook type fastener material attached to its flap by stitching 182. Although not shown in FIGS. 7 or 8 for simplicity, the upper and lower support arms of the knee joint support extend into the pocket regions of the upper and lower portions 170 and 174 of the second flexible enclosure 168, and the flap on the enlarged region 178 extends around both sides of the hinged portion of the brace. The fastener 180 is then adhered to the terry cloth material on the outside of the second flexible enclosure to retain the enclosure around the hinged portion of the brace. As shown best in FIG. 7, the two knee joint supports extend parallel to one another, separated by a distance sufficient to retain both knee joint supports adjacent opposite sides of the knee joint during use. The flexible upper straps are attached to each other preferably by two layers of a Velcro hook fastener material 184 at the ends of the long and short upper straps 130 and 104. These fasteners allow the long and short straps to attach to the terry cloth outer faces of the short and long upper straps, respectively. This permits infinite adjustment of the distance between the two pockets on the combined upper strap. Similarly, elongated Velcro-type hook fasteners 186 at the ends of the long and short lower straps 132 and 106 are adhered to the terry cloth outer faces of the short and long lower straps for releasably fastening the two lower straps together. This holds the lower support arms of the two braces at a selected distance apart. The free end of the long upper strap has an elongated fastener 188 preferably of Velcro-type hook fastener, and the long lower strap has a similar fastener 190. This fasteners at the free ends of the long upper and lower straps are used to retain tension after the upper and lower straps are wrapped around the upper and lower leg. These hook-type fasteners are adhered to the terry cloth outer faces of the long upper and lower straps during use.

FIG. 8 best illustrates the brace of FIG. 7 with the combined upper straps in a position for wrapping around the upper leg and the combined lower straps in a position for being wrapped around the lower leg. This view also illustrates the enlarged center regions of the flexible enclosures 150 and 178 being wrapped around both sides of the hinged portions of the knee joint supports which are inserted in the upper and lower pockets formed on opposite sides of the brace.

The brace of FIGS. 7 and 8 is an entirely flexible brace that is light in weight and comfortable to wear It also provides a goods means of support for opposite sides of the knee joint. Because of its light weight and comfort, the brace is particularly useful as a preventive device that can be worn for long periods of time comfortably while providing the support necessary to prevent injuries to the knee joint.

FIGS. 9 through 12 illustrate an articulated non-pinching knee joint support 192 which comprises an improvement over the knee joint support illustrated in FIGS. 1 and 2. The non-pinching knee joint support includes a stepped upper support arm 194 and a stepped lower support arm 196. The upper and lower support arms are preferably made from a lightweight high impact plastic. The upper support arm 194 includes an offset lower section 194' and the lower support arm 196 includes an offset upper section 196'. The support arms also include elongated molded plastic embossments extending from the principal portion of each support arm across the stepped region to the offset portion of the support arm. These embossments include a pair of spaced apart and parallel elongated outer embossments 198 projecting outwardly from the outer face of the upper support arm, and a pair of spaced apart and parallel elongated inner embossments 200 projecting outwardly from the inside face of the upper support arm.

As shown best in the side view of FIG. 10, the outer embossments 198 rigidly reinforce the stepped region of the support arm at a different elevation from the inner embossments 200 which reinforce a lower portion of the stepped region on the inside face of the support arm. Similarly, the lower support arm includes a pair of spaced apart and parallel outer embossments 202 projecting from the outer face of the lower support arm. A similar pair of rigid elongated plastic embossments 204 project from the inside face of the lower support arm. The reinforcing embossments provide lateral rigidity to the support arms by restricting bending of the offset portions of the support arms relative to the principal portions of the support arms. The embossments also provide a level of torsional rigidity. The reinforcing embossments provide the rigidity necessary for the support arms to act as lightweight impact-resistive members that prevent the transfer of impact to the ligaments of the knee joint during use. A similar knee brace without the reinforcing embossments is too flexible, and therefore transfers a substantial amount of the impact blow to the side of the knee joint, as opposed to resisting a useful level of impact energy.

The upper support arm 194 has a curved bottom edge 206, and the lower support arm 196 has a curved top edge 208. Both edges engage one another when the support arms are both in a generally upright position as shown in FIGS. 9 through 12. In this upright relative position, the long axes of the two support arms are aligned in essentially a vertical axis. Both adjacent curved edges taper away from one another in the direction toward which each arm is free to rotate. This gradually widened tapered open space between the adjacent edges of the arms allows each arm to pivot through a full 180° angle relative to the other arm, or it allows the two arms to pivot together through combined angles that total 180°. For instance, in a manner similar to the knee joint support of FIGS. 1 and 2, the upper support arm can pivot 90° relative to the lower arm, and the lower arm then can pivot up to the other arm until the two arms are essentially parallel to one another. The curved edges 206 and 208 are arranged so they rotate into rigid engagement with one another as the two arms rotate to the vertical upright position shown in FIGS. 9 through 12. As the two arms arrive at this position with respect to one another, the two curved edges come into contact and prevent further rotation of each arm relative to the other in the same direction of rotation. Thus, by limiting rotation of the two support arms past their upright positions, the contacting edges act as a stop. When used in a knee brace, the stop can inhibit hyperextension injuries to the knee joint, as described in greater detail above.

The upper and lower support arms are interconnected by a non-pinching X-shaped hinge system which includes an elongated flat, rigid, first stabilizing hinge plate 210 hinged to the outside of the offset lower portion 194' of the upper support arm 194 and hinged at its opposite end to the outside of the offset upper portion 196' of the lower support arm 196. The X-shaped hinge system also includes an elongated flat, rigid, second stabilizing hinge plate 212 hinged to the inside of the offset lower portion 194' of the upper support arm and hinged at its opposite end to the inside portion of the offset upper portion 196' of the lower support arm. A front pivot pin 214 pivotally connects the first hinge plate 210 to a front portion of the upper support arm, and a rear pivot pin 218 pivotally connects a lower portion of the first hinge plate to a rear portion of the lower support arm. Similarly, an upper pivot pin 216 pivotally secures an upper portion of the second hinge plate to the rear of the offset lower portion of the upper support bar 194, and a lower pivot pin 220 pivotally secures the lower portion of the second hinge plate to a forward region of the lower support arm 196. The first and second hinge plates are on opposite sides of the offset portions of the upper and lower support arms. Thus, when the knee supporting brace is viewed from the side, as either in FIG. 9 or 11, the two hinge plates intersect to form a generally X-shaped hinge system. The first hinge plate overlies the flat outer faces of the lower and upper offset portions of the upper and lower support arms, respectively; and the second hinge plate overlies the flat inside faces of the offset lower and upper portions of the upper and lower support arms, respectively. The hinge plates are preferably made from a rigid metal such as stainless steel. Both hinge plates overlie a substantial surface area of the adjacent offset portions of the upper and lower support arms so as to provide substantial rigidity for the articulated knee joint support in the offset regions adjacent the knee.

The first and second hinge plates 210 and 212 are shaped and arranged in a non-pinching combination, so that during rotation of the upper and lower support arms, any object entering the space between the adjacent ends of the rotating support arms is not subject to pinching. The first hinge plate 210 is generally triangular shaped, having a narrow-width upper portion 222 to which the front upper pivot pin 214 is attached, a generally narrow-width lower portion 224 to which the rear pivot pin 218 is attached, and a wider intermediate region 226 toward which the narrow-width end portions of the plate taper wider so as to cover the juncture between the contacting stop edges 206 and 208 of the support arms when the support arms are in the upright position shown in FIGS. 9 through 12. Similarly, the second hinge plate 212 is generally triangular shaped, having a narrow-width upper portion 228 to which the upper pivot pin 216 is attached, a generally narrow-width lower portion 230 to which the lower pivot pin 220 is attached, and a wider intermediate portion 232 that covers the juncture between the adjacent edges 206 and 208 of the support arms when the arms are in the upright position. The apex 234 of the first hinge plate 210 is located at an elevation below the contact point between the bottom edge 206 of the upper arm and the upper edge 208 of the lower arm, when both arms are in the upright position. Similarly, the apex 236 of the rear hinge plate 212 is located at an elevation above the contact point between the bottom edge 206 and the upper edge 208 of the arms. With the arms in the upright position, neither apex of the triangular hinge plates protrudes appreciably from the front edges of the upper and lower support arms. This is best shown at the left side of FIG. 9 and the right side of FIG. 11 where the apex portions of the hinge plates are shown projecting a slight distance beyond the front edges of the support arms.

FIGS. 13 and 14 illustrate the relative positions of the hinge plates as the upper and lower support arms rotate toward each other away from the upright position shown in FIGS. 9 through 12. When each arm of the brace has rotated through about a 45° angle as shown in FIG. 13, the wider intermediate portions of the triangular hinge plates project into and cover the resulting open space between the adjacent edges 206 and 208 of the support arms. The apex portions of the first and second hinge plates are shown projecting into the wide portion of the open space between the support arms. The narrowest space between the adjacent ends of the support arms is covered by the hinge plates. As each arm of the brace has rotated through nearly 90°, as illustrated in FIG. 14, the wider intermediate portions of the trinagular hinge plates continue to project in front of and cover the narrowest space between the adjacent edges 206 and 208 of the support arms. In the view shown in FIG. 14, the apex portions of the outer and inner hinge plates have bypassed one another from the positions they occupied in the positions shown in FIG. 13.

Without the non-pinching hinge plates, pinching could occur when an object protrudes into the space between the adjacent edges 206 and 208 of the support arms. As the support arms rotate from an angular position (such as those shown in FIG. 13 or 14) toward the upright position shown in FIGS. 9 through 12, the adjacent edges 206 and 208 move closer together. A person's finger or an article of clothing in the space between the edges of the support arms could be pinched as these edges of the support arms rotate closer together, toward the upright position. The overlapping triangular hinge plates prevent such pinching from occurring. For instance, as the support arms rotate from the position shown in FIG. 14 to the position shown in FIG. 13 and then to the position shown in FIGS. 9 and 11, an article in the space between the adjacent edges 206 and 208 could be pinched, since those edges can act as jaws by squeezing an object between the arms as the arms rotate closer together. However, the protruding widened portions of the hinge plates, and particularly the apex portions of the hinge plates, project over both sides of the open space between the edges of the support arms to cover most of the open area between the two support arms. They prevent any object from entering or being caught in the narrow space between the ends of the rotating support arms. As the support arms rotate toward the position where pinching could occur, the widened portions of the triangular hinge plates progressively move outwardly and overlap the front edges of the support arms, at the entrance to the point where pinching would occur. During the full range of travel of the upper and lower support arms, the hinge plates move so as to cover the narrowest open space between the arms, and this movement prevents articles from effectively entering the narrow space where pinching could occur.

In addition to preventing pinching by the contacting edges 206 and 208 at the front of the upper support arms, the hinge plates also prevent pinching from occurring on the opposite side of the open space between the support arms. In this instance, the rear edges 238 and 240 of the outer and inner hinge plates cover the entrance to the space between the rotating upper and lower support arms on the rear side of the brace. This also prevents articles from entering that portion of the open space where pinching might occur.

The non-pinching hinge arrangement shown in FIGS. 9 through 15 can be used in the same applications as the brace shown in FIGS. 1 and 2 and can be substituted in the various knee braces described above. The brace shown in FIGS. 9 through 15 does not include fastening means adhered directly to the inner or outer faces of the upper and lower support arms. In this embodiment, the upper and lower support arms are curved in cross section, as shown best in FIG. 15, for fitting the contour of the sides of the upper and lower legs during use.

What is claimed is:

1. A knee joint support comprising:
   an upper support arm having a lower end,
   a lower support arm having an upper end,
   a first hinge bar pivotally secured to a lower portion of the upper support arm and to an upper portion of the lower support arm, and
   a second hinge bar pivotally secured to the lower portion of the upper support arm to pivot about an axis forward of the pivot axis between the first hinge bar and the upper support arm,
   the second hinge bar being pivotally secured to the upper portion of the lower support arm to pivot about an axis between the pivot axis between the first hinge bar and the lower support arm,
   the first and second hinge bars being positioned on opposite sides of the upper and lower support arms,
   the first and second hinge bars allowing relative rotation of the upper and lower support arms about a polycentric axis while resisting forward or rearward sliding movement of each bar relative to the other,
   the lower and upper ends of the upper and lower support arms, respectively, being positioned so they are spaced apart as the upper and lower support arms rotate though an angle formed by the two arms, the lower and upper ends of the upper and lower support arms rotating into contact with one another when relative rotation of the upper and lower arms reaches a substantially upright position between the two arms for resisting said relative rotation beyond the substantially upright position, the hinge bars each having a widened central portion of sufficient width to overlap the space formed between the lower and upper ends of the support arms in their angular positions and to also overlap the contacting lower and upper ends of the support arms on said opposite sides of the support arms when the support arms rotate to said upright position of the two arms, for preventing an object entering the space formed between the ends of the support arms from being pinched by the contacting ends of the support arms as the arms rotate into their upright position,
   the upper and lower support arms being adapted for mounting adjacent the upper and lower leg of a user with the first and second hinge bars adjacent the knee joint, so that the support arms resist forward or rear sliding movement of the user's upper leg relative to the lower leg, or vice versa, and so that the contact between the ends of the support arms resists rotation of the upper and lower leg beyond said substantially upright position.

2. Apparatus according to claim 1 in which the lower and upper portions of the upper and lower support arms are offset from upper and lower portions of the upper and lower support arms, respectively.

3. Apparatus according to claim 2 in which each hinge bar crosses the pivot axis of the other bar's connection to the same support arm during angular rotation of the upper and lower support arms.

4. Apparatus according to claim 3 in which the upper and lower support arms are made of hard plastic, and the first and second hinge bars are made of metal.

5. Apparatus according to claim 1 in which the lower and upper portions of the upper and lower support arms are offset from upper and lower portions of the upper and lower support arms, and the upper and lower support arms are made of a hard plastic and include reinforcing embossments extending from the upper portion of the upper support arm to the offset portion of the upper support arm and extending from the lower portion of the lower support arm to the offset portion of the lower support arm.

6. Apparatus according to claim 1 in which the hinge bars are each substantially triangular in shape with the apex portion of the triangles projecting so as to overlap the contacting lower and upper ends of the upper and lower support arms.

7. Apparatus according to claim 1 in which the lower and upper ends of the support arms contact one another along the front edges of the upper and lower support arms, respectively, and the widened portions of the hinge bars overlap the contacting front edges of the support arms on the opposite sides of the support arms.

8. Apparatus according to claim 1 in which the hinge bars are sufficiently wide to overlap the narrowest spacing between the adjacent ends of the support arms during their rotation through said angle.

9. Apparatus according to claim 1 in which the lower and upper portions of the upper and lower support arms, respectively, are offset laterally from upper and lower portions of the upper and lower support arms, respectively.

10. Apparatus according to claim 9 in which the upper and lower support arms are made of hard plastic and include reinforcing embossments extending from the upper portion of the upper support arm to the offset portion of the upper support arm and extending from the lower portion of the lower support arm to the offset portion of the lower support arm.

11. A knee stabilizing orthosis comprising:
    a pair of knee joint supports for supporting lateral and medial sides of the knee joint, each such knee joint support comprising: (a) an upper support arm having a lower end, (b) a lower support arm having an upper end, (c) a first hinge bar pivotally secured to a lower portion of the upper support arm and to an upper portion of the lower support arm, and (d) a second hinge bar pivotally secured to the lower portion of the upper support arm to pivot about an axis forward of the pivot axis between the first hinge bar and the upper support arm; in which the second hinge bar is pivotally secured to the upper portion of the lower support arm to pivot about an axis behind the first pivot axis between the first hinge bar and the lower support arm, the first and second hinge bars being positioned on opposite sides of the upper and lower support arms, the first and second hinge bars allowing relative rotation of the upper and lower support arms about a polycentric axis while resisting forward or rear sliding movement of each bar relative to the other bar; the lower and upper ends of the upper and lower support arms, respectively, being positioned so they are spaced apart as the upper and lower support arms rotate through an angle formed by the two arms, the ends rotating into contact with one another when relative rotation of the upper and lower bars reaches a substantially upright position between the two bars for resisting said relative rotation beyond said substantially upright position;

the hinge bars each having a widened central portion of sufficient width to overlap the space formed between the lower and upper ends of the support arms in their angular positions and to overlap the contacting lower and upper ends of the support arms on said opposite sides of the support arms when the arms rotate to said upright position of the two bars, for preventing an object entering the space formed between the ends of the support arms from being pinched by the contacting ends of the support arms as the arms rotate into their upright position; and means for securing the upper and lower support arms adjacent the upper and lower legs of a user, comprising (a) a bendable upper reinforcing member for conforming to the anatomical shape of the lower leg, (b) a bendable lower reinforcing member for conforming to the anatomical shape of the lower leg, (c) means rigidly securing the upper and lower support arms of one of said knee joint supports to the lateral sides of the upper and lower reinforcing members, (d) means rigidly securing the upper and lower support arms of said knee joint support to the medial sides of the upper and lower reinforcing members, (e) upper fastening means for extending around the upper leg for attaching the upper reinforcing member to the upper leg, and (f) lower fastening means for extending around the lower leg and for attaching the lower reinforcing member around the lower leg.

12. Apparatus according to claim 11 including flexible padding on the upper and lower reinforcing members, means for releasably securing the upper fastening means to the flexible padding on the upper member, and means for releasably securing the lower fastening means to the flexible padding on the lower member.

13. Apparatus according to claim 11 in which the upper reinforcing member extends around about half the upper leg and the lower reinforcing member extends around about half the lower leg, and the upper fastening means comprises a stretchable upper cuff extending around the upper leg and having means for releasably securing it to the padded upper member, and the lower fastening means comprises a stretchable lower cuff extending around the lower leg and having means for securing it to the padded lower member.

14. Apparatus according to claim 13 in which the upper and lower cuffs are releasably attachable to padded regions inside the upper and lower members.

15. Apparatus according to claim 11 in which the lower and upper portions of the upper and lower support arms are offset laterally from upper and lower portions of the upper and lower support arms, respectively.

16. Apparatus according to claim 15 in which each hinge bar pivots across the pivot axis of the other bar's connection to the same support arm during angular rotation of the upper and lower arms.

17. Apparatus according to claim 11 in which the lower and upper portions of the upper and lower support arms are offset from the upper and lower portions of the upper and lower support arms, and the upper and lower support arms are made of hard plastic and include reinforcing embossments extending from the upper portion of the upper support arm to the offset portion of the upper support arm and extending from the lower portion of the lower support arm to the offset portion of the lower support arm.

18. An infinitely adjustable, highly flexible lightweight knee joint supporting orthosis comprising:

a lateral brace having a rigid upper support arm for overlying the lateral side of the upper leg, a rigid lower support arm for overlying the lateral side of the lower leg, and hinge means attaching respective ends of the upper and lower support arms for controlling the angle through which the upper and lower support arms rotate during angular motion of the knee joint;

a medial brace having a rigid upper support arm for overlying the medial side of the upper leg, a rigid lower support arm for overlying the medial side of the lower leg, and hinge means attaching the respective ends of the upper and lower support arms for controlling the angle through which the upper and lower support arms rotate during angular motion of the knee joint;

a lateral flexible padding having (a) an upper pocket for holding the upper support arm of the lateral brace, (b) a lower pocket for holding the lower support arm of the lateral brace, (c) an elongated sleeve section between the upper pocket and the lower pocket for overlying one side of the hinge means of the lateral brace and for overlying the opposite side of the hinge means to enclose the hinge means with flexible padding, (d) releasable fastening means for securing the flexible padding of the sleeve section around the hinge means, (e) an elongated upper cuff extending laterally away from the upper pocket, and (f) an elongated lower cuff extending laterally away from the lower pocket;

a medial flexible padding having (a) an upper pocket for holding the upper support arm of the medial brace, (b) a lower pocket for holding the lower support arm of the medial brace, (c) an elongated sleeve section extending between the upper pocket and the lower pocket for overlying one side of the hinge means of the medial brace and for extending around and overlying the opposite side of the hinge means of the medial brace to enclose the hinge means with flexible padding, (d) releasable fastening means for securing the flexible padding of the sleeve section around the hinge means of the medial brace, (e) an elongated upper cuff extending laterally away from the upper pocket, and (f) an elongated lower cuff extending laterally away from the lower pocket;

fastening means on the upper lateral and medial cuffs for releasably securing the cuffs circumferentially in an infinitely adjustable length around the upper leg and for holding tension around the circumferentially wrapped upper leg;

fastening means on the lower lateral and medial cuffs for releasably securing the cuffs in an infinitely adjustable length wrapped circumferentially around the lower leg and for holding tension around the circumferentially wrapped lower leg;

and in which the lateral brace and the medial brace each having hinge means comprising:

a first hinge bar pivotally secured to a lower portion of the upper support arm and to an upper portion of the lower support arm, a second hinge bar pivotally secured to the lower porton of the upper support arm to pivot about an axis forward of the pivot axis between the first hinge bar and the upper support arm, the second hinge bar being pivotally secured to the upper portion of the lower support arm to pivot about an axis behind the pivot axis between the first hinge bar and the lower support arm, the first and second hinge bars being positioned on opposite sides of the upper and lower support arms, the first and second hinge bars allowing relative rotation of the upper and lower support arms about a polycentric axis while resisting forward or rearward sliding movement of each arm relative to the other, the lower and upper ends of the upper and lower support arms, respectively, being positioned so they are spaced apart as the upper and lower support arms pivot through an angle formed by the two bars, the ends rotating into contact with one another when relative rotation of the upper and lower bars reaches a substantially upright position between the two bars for resisting said relative rotation beyond said substantially upright position, the hinge bars each having a widened central portion of sufficient width to overlap the space formed between the lower and upper ends of the support arms in their angular positions and to overlap the contacting lower and upper ends of the support arms on said opposite sides of the support arms when the support arms rotate to said upright position of the two bars, for preventing an object entering the space formed between the ends of the support arms from being pinched by the contacting ends of the support arms as the support arms rotate into their upright position.

19. Apparatus according to claim 18 in which the lateral brace and the medial brace each have hinge means comprising:

a first hinge bar pivotally secured to a lower portion of the upper support arm and to an upper portion of the lower support arm, a second hinge bar pivotally secured to the lower portion of the upper support arm to pivot about an axis forward of the pivot axis between the first bar and the upper support arm, the second hinge bar being pivotally secured to the upper portion of the lower support arm to pivot about an axis behind the pivot axis between the first bar and the lower support arm, the first and second hinge bars allowing relative rotation of the upper and lower support arms about a polycentric axis while resisting forward or rearward sliding movement of each bar relative to the other, the lower and upper ends of the upper and lower support arms, respectively, being positioned so they rotate into contact with one another when relative rotation of the upper and lower bars reaches a substantially upright position between the two bars for resisting said relative rotation beyond said substantially upright position.

20. Apparatus according to claim 19 in which lower and upper portions of the upper and lower support arms are laterally offset from upper and lower portions of the upper and lower support arms, respectively.

21. Apparatus according to claim 19 in which the lower and upper portions of the upper and lower support arms are offset from upper and lower portions of the upper and lower support arms, and upper and lower support arms are made of hard plastic and include reinforcing embossments extending from the upper portion of the upper support arm to the offset portion of the upper support arm and extending from the lower portion of the lower support arm to the offset portion of the lower support arm.

22. Apparatus according to claim 19 in which the hinge bars are each substantially triangular in shape with the apex portions of the triangles projecting so as to overlap the contacting lower and upper ends of the upper and lower support arms.

23. A knee joint support comprising:
an upper support arm having a lower end,
a lower support arm having an upper end,
a first hinge bar pivotally secured to a lower portion of the upper support arm and to an upper portion of the lower support arm, and
a second hinge bar pivotally secured to the lower portion of the upper support arm to pivot about an axis forward of the pivot axis between the first hinge bar and the upper support arm,
the second hinge bar being pivotally secured to the upper portion of the lower support arm to pivot about an axis behind the pivot axis between the first hinge bar and the lower support arm,
the lower and upper portions of the upper and lower support arms being offset laterally from upper and lower portions of the upper and lower support arms, respectively;
the first and second hinge bars being positioned on opposite sides of the offset portions of the support arms with axes that cross one another;
the first and second hinge bars allowing relative rotation of the upper and lower support arms about a polycentric axis while resisting forward or rearward sliding movement of each bar relative to the other;
the lower and upper ends of the upper and lower support arms, respectively, being positioned so they are spaced apart as the upper and lower support arms pivot through an angle formed by the two arms, the upper and lower ends of the support arms rotating into contact with one another when the relative rotation of the upper and lower support arms reaches a substantially upright position between the two arms, for resisting said relative rotation of the arms beyond their substantially upright position;
and in which the hinge bars are each of sufficient width to overlap the space formed between the lower and upper ends of the support arms in their angular position and to overlap the contacting lower and upper ends of the support arms on said opposite sides of the support arms when the arms rotate into said upright position, for preventing an object entering the space formed between the ends of the support arms from being pinched by the contacting ends of the support arms as they rotate into their upright position.

24. Apparatus according to claim 23 in which the upper and lower support arms are made of a hard plastic and include reinforcing embossments extending from the upper portion of the upper support arm to the offset portion of the upper support arm and extending from the lower portion of the lower support arm to the offset portion of the lower support arm.

25. Apparatus according to claim 23 in which the hinge bars are each substantially triangular in shape with the apex portion of the triangles projecting so as to overlap the contacting lower and upper ends of the upper and lower support arms.

26. Apparatus according to claim 23 in which the lower and upper ends of the support arms contact one another along the front edges of the upper and lower support arms, respectively, and the hinge bars overlap the contacting front ends of the support arms on opposite sides of the support arms.

27. Apparatus according to claim 23 in which the hinge bars are sufficiently wide to overlap the narrowest spacing between the adjacent ends of the support arms during their rotation through said angle.

* * * * *